(12) United States Patent
Willis et al.

(10) Patent No.: US 9,155,840 B1
(45) Date of Patent: Oct. 13, 2015

(54) SYRINGE ASSEMBLY INCLUDING VOLUME INDICATING INDICIA

(75) Inventors: Phillip Minyard Willis, Duluth, GA (US); Audeliz Crespo, Jr., Alpharetta, GA (US)

(73) Assignee: PERRIGO DIABETES CARE, LLC, Allergan, MI (US)

(*) Notice: Subject to any disclaimer, the term of this patent is extended or adjusted under 35 U.S.C. 154(b) by 824 days.

(21) Appl. No.: 13/323,997

(22) Filed: Dec. 13, 2011

Related U.S. Application Data

(63) Continuation-in-part of application No. 13/086,108, filed on Apr. 13, 2011.

(51) Int. Cl.
*A61M 5/31* (2006.01)
*A61M 5/178* (2006.01)
*A61M 5/36* (2006.01)

(52) U.S. Cl.
CPC .............. *A61M 5/31* (2013.01); *A61M 5/178* (2013.01); *A61M 5/36* (2013.01); *A61M 2005/3125* (2013.01)

(58) Field of Classification Search
CPC ............... A61M 5/178; A61M 2005/3125; A61M 2005/3126; A61M 2205/33; A61M 2205/58; A61M 2205/583; A61M 2205/584; A61M 2205/585
USPC ........................ 604/187, 189, 207, 208, 260
See application file for complete search history.

(56) References Cited

U.S. PATENT DOCUMENTS

| | | | | |
|---|---|---|---|---|
| 182,192 | A | * | 9/1876 | Hicks et al. ................. 73/327 |
| 330,621 | A | * | 11/1885 | Reichardt ................... 604/207 |
| 2,303,154 | A | | 11/1942 | Armstrong |
| 2,888,015 | A | * | 5/1959 | Hunt ........................... 604/207 |
| 3,774,603 | A | * | 11/1973 | McPhee ...................... 604/246 |
| 4,452,251 | A | * | 6/1984 | Heilman ...................... 600/432 |
| 5,062,828 | A | * | 11/1991 | Waltz ............................ 73/327 |
| 5,242,405 | A | * | 9/1993 | Howe .......................... 604/125 |
| 5,383,858 | A | * | 1/1995 | Reilly et al. ................. 604/152 |
| 6,120,481 | A | * | 9/2000 | Rennert et al. .............. 604/187 |
| 6,315,760 | B1 | * | 11/2001 | Sharp .......................... 604/189 |
| 2002/0087121 | A1 | * | 7/2002 | Slishman ..................... 604/189 |
| 2008/0018814 | A1 | | 1/2008 | Tsai et al. |
| 2008/0138387 | A1 | * | 6/2008 | Machiraju ................... 424/446 |
| 2008/0188814 | A1 | * | 8/2008 | Lavi-Loebl et al. .......... 604/189 |
| 2009/0139126 | A1 | * | 6/2009 | Alipour ...................... 40/642.02 |

\* cited by examiner

*Primary Examiner* — Andrew Gilbert
(74) *Attorney, Agent, or Firm* — Breiner & Breiner, L.L.C.

(57) ABSTRACT

A syringe assembly for the delivery of medications or other liquid contents including an elongated hollow body at least partially formed by transparent material and including an indicia assembly for indicating volume measurement of and/or the existence of a void within the contained liquid. The indicia assembly includes a first indicia section and a second indicia section extending along a common wall portion, wherein a segregating section is disposed between the first and second indicia section and is structured to visually segregate the visual markings of the first and second indicia sections while being sufficiently contrasted in appearance to facilitate the independent viewing thereof. The first and second indicia sections are disposed and structured to be independently viewed along different lines of sight. One or more indicators may also be disposed on the syringe body to facilitate the determination of voids with the body interior.

11 Claims, 5 Drawing Sheets

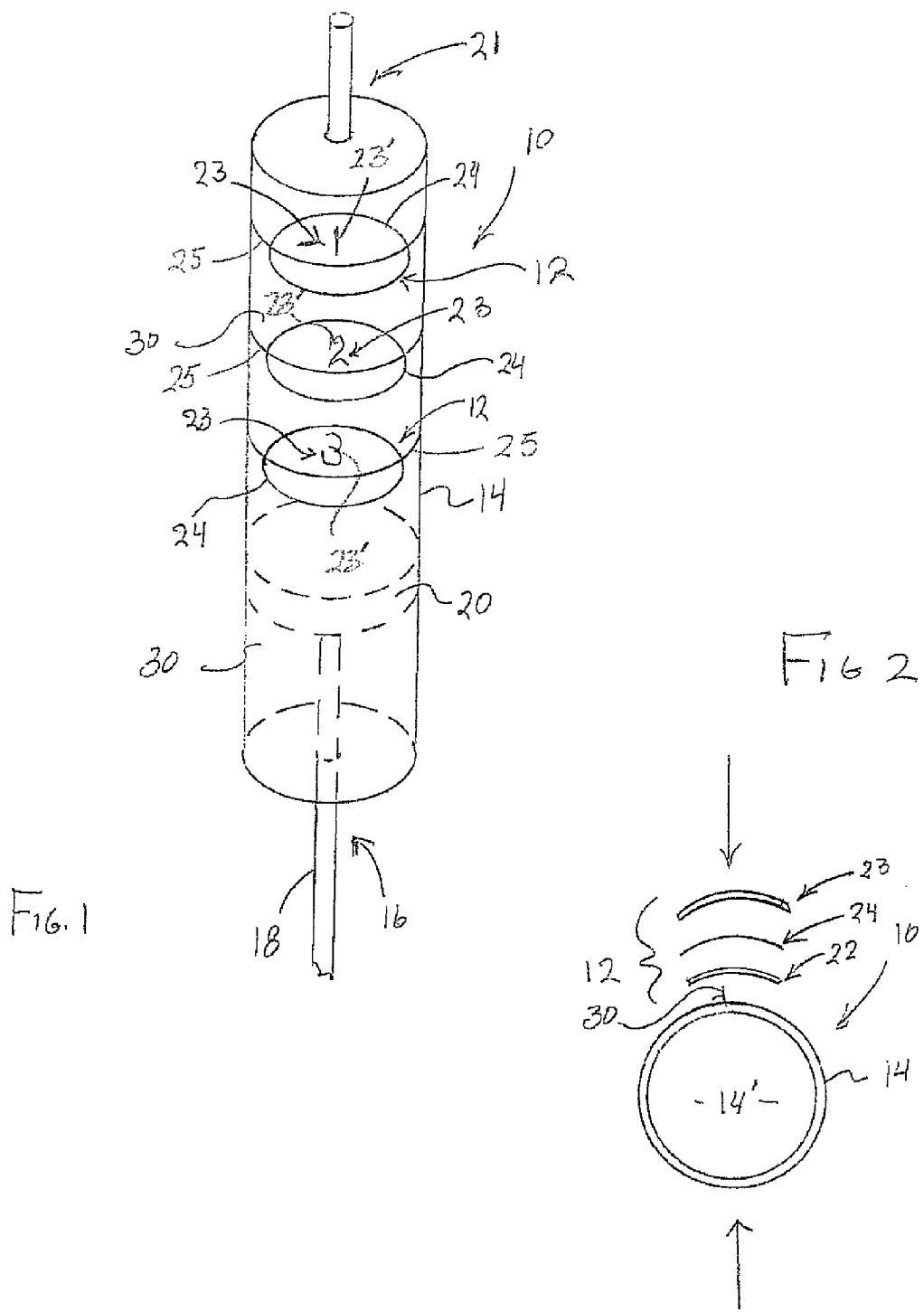

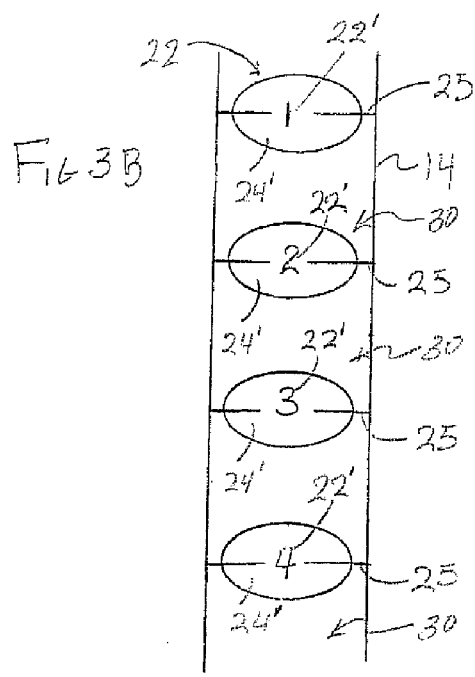
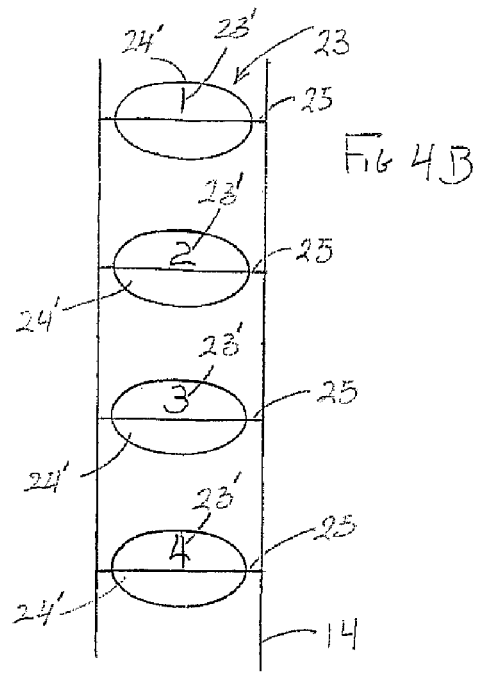
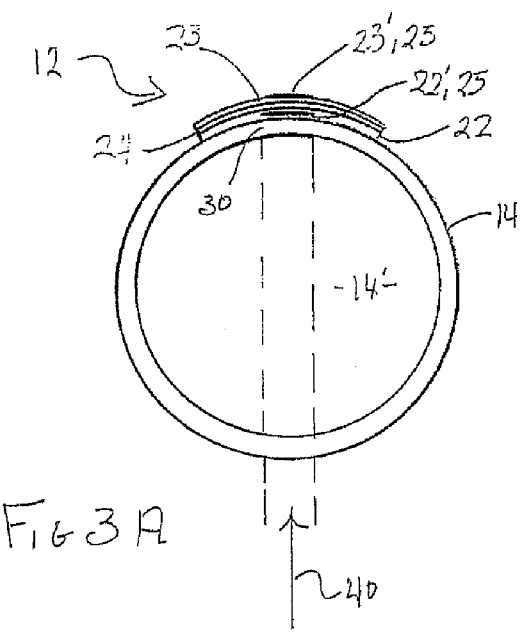
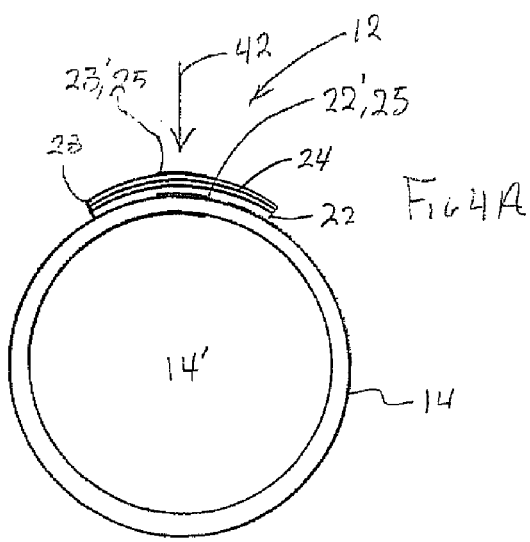

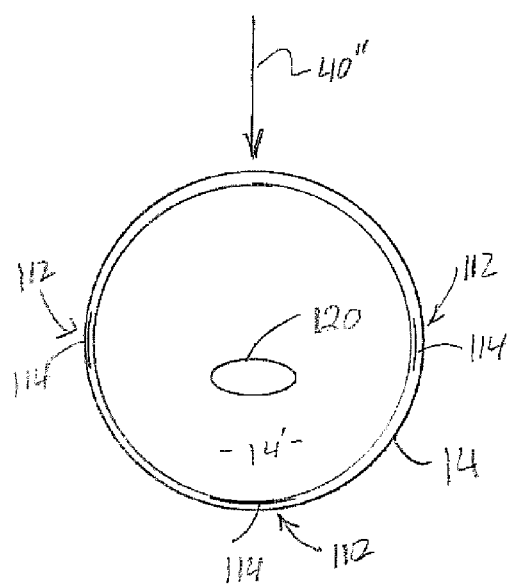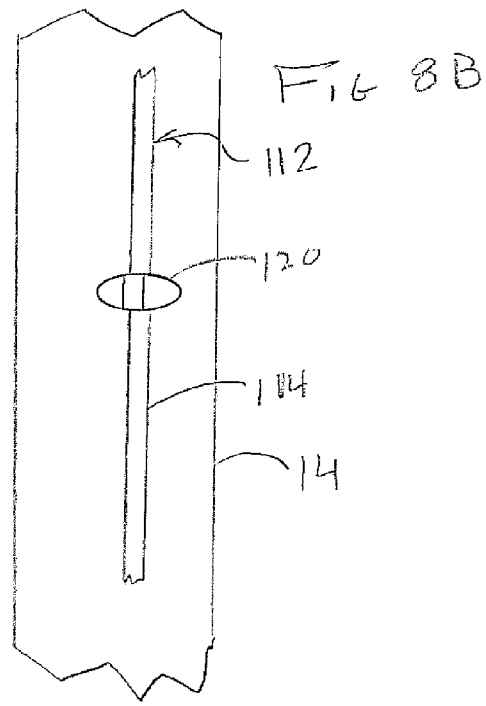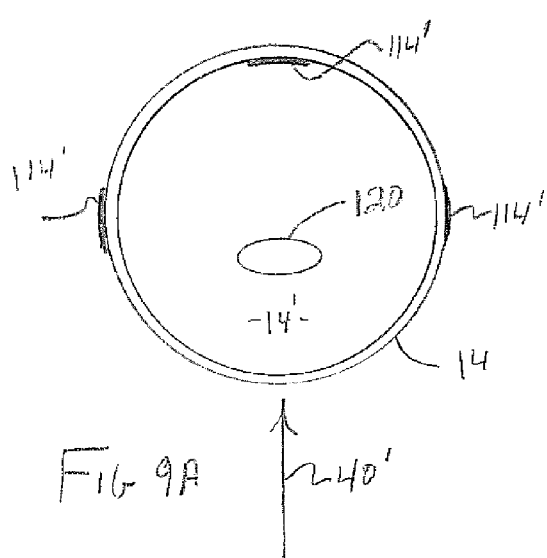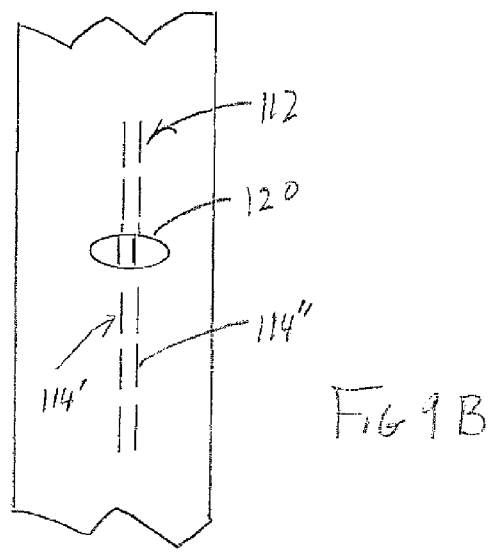

SYRINGE ASSEMBLY INCLUDING VOLUME INDICATING INDICIA

CLAIM OF PRIORITY

The present application is a continuation-in-part application of previously filed, now pending application having Ser. No. 13/086,108, filed on Apr. 13, 2011 incorporated herein by reference.

BACKGROUND OF THE INVENTION

1. Field of the Invention

This invention is directed to a syringe structure including an assembly of indicia extending along a common wall portion of the syringe barrel and including a first indicia section and a second indicia section. A segregating section enables a contrast in the appearance of the indicia sections, thereby facilitating a viewing of the first indicia section and common wall portion through the interior of the syringe barrel and a viewing of the second indicia section from an exterior of the syringe barrel, along a line of sight directed towards an exterior surface of the common wall portion.

2. Description of the Related Art

A syringe, as commonly used in the medical profession, typically includes an elongated, hollow interior body or barrel having one end structured to receive a needle or alternatively include a converging luer, nozzle or like structure. The opposite end of the barrel is adapted to movably receive a plunger structure on the interior thereof. Moreover, the plunger structure includes a head portion movably disposed in fluid sealing engagement with interior surfaces of the barrel. The plunger also includes an elongated rod wherein the outer or free end thereof is structured to facilitate manipulation by a user's hand and/or fingers. As a result of the interaction between the plunger structure and the syringe barrel, a liquid medication or other fluid material may be drawn into the interior of the barrel and forced outwardly therefrom for delivery to a patient, IV container, etc.

As should be apparent, a determination of the measurement of the volume or quantity of the liquid contents within the barrel is frequently critical. Such an accurate determination is specifically, but not exclusively, required when a medication is being delivered to a patient. Moreover, there are situations where self medication is a common occurrence, such as in the case of an individual suffering from diabetes, wherein blurred or diminished vision is a recognized symptom. In cases such as these the accurate determination of the quantity of medication contained within the syringe may be critical. In order to overcome problems associated with accurate volume measurement of the contents of a syringe barrel, common structural features of syringe structures have included the provision of indicia disposed on the barrel in a manner and location which hopefully facilitates its reading and/or visual observation.

Accordingly in order to facilitate ease of reading the included volume measuring indicia, various structures and/or techniques have been applied to the manufacture of medical syringes which establish a sufficient visual contrast between the indicia and the structure of the barrel and/or the stopper or head of the plunger assembly. By virtue of such contrast, accurate determination of volume measurement of the contained fluid within the barrel is more reliable and efficiently accomplished. In addition, conventional syringes of the type set forth hereinafter have included various structures to improve a reliable reading, through visual determination, of the volume measuring indicia. In most instances, the material from which the syringe barrel is formed is transparent and the indicia formed on some portion of the barrel typically includes a contrasting color or other appearance which attempts to render visual observation of the indicia more efficient and effective.

In addition, more recent structuring of syringe assemblies have included the formation of various portions of the plunger specifically including, but not limited to, the plunger head or stopper being formed of a black or darkly colored plastic or like material. In contrast, the arm or shaft of the plunger may be typically formed of a white material, wherein the white color of the plunger arm enhances the visual contrast between this portion of the plunger and the normally darker color of the indicia. However, due to the fact that the volume measurement of the contents of the barrel is frequently, if not exclusively, determined by an aligned orientation of the distal extremity of the plunger head with the indicia, the black or darker color of the plunger head, such as when it is aligned with the darkened indicia, makes it difficult to accurately read the aligned indicia.

Even in light of the various attempted advances in conventional syringe design and manufacture, there still remains a need for improvements specifically, but not exclusively, directed to the structuring of an improved syringe assembly. Proposed improvements should include various operative and/or structural features which facilitate the filling, dispensing and determining of accurate quantities liquid medication and/or other fluid. Such a proposed and improved syringe assembly should therefore include an indicia assembly which accomplishes a reliable and efficient determination of volume measurement. Moreover, such efficient determination should include situations which allow a user of the syringe assembly to view the indicia from each of a plurality of different viewing vantage points. More specifically an improved and proposed syringe assembly and included indicia assembly should facilitate accurate reading of the indicia from at least two different locations of the individual. Moreover, the two different locations may include a viewing along a line of sight passing through the interior of the syringe barrel and the liquid contents contained therein. Alternately, the two different locations may include viewing from an exterior of the syringe barrel, along a line of sight directed towards an exterior surface of the improved syringe barrel. Due to the structuring of the improved indicia assembly, such different viewing locations may allow for an exclusive reading of a predetermined portion of the indicia assembly, wherein different portions of the improved indicia assembly can not be viewed from both of the two different locations.

In addition, the proposed and improved indicia assembly will significantly increase the visual contrast of the indicia assembly and the syringe barrel and/or the plunger structure, thereby enabling a significant savings in cost of material while maintaining a reliable accuracy in determining volume measurement. More specifically, the enhanced contrast of the indicia assembly relative to a remainder of the syringe assembly enables the plunger structure to be formed from other recycled plastic material since the necessity of maintaining the aforementioned bright or white coloring of the plunger structure is no longer a requirement. Therefore, recycled plastic material can be used to form the plunger structure which may result in a plunger structure having a less than totally white appearance, such as a substantially gray-colored appearance. As a result, the plunger structure will not have to be formed from a uniquely preferred plastic material, but rather can be formed from a recycled plastic material resulting in significant savings in material costs.

SUMMARY OF THE INVENTION

The present invention is directed to a syringe assembly which, as conventionally used, is structured to dispense liquid medication or other fluids. In addition, the syringe assembly includes an elongated hollow body or syringe barrel at least partially formed of a transparent material. As is commonly recognized, the transparency of the material from which the barrel is formed facilitates the viewing and volume determination of the medication or other fluid disposed within the barrel. As is also well known, the syringe assembly may be associated with some type of dispensing structure such as a plunger having a head disposed at one end thereof and a gripping or engaging structure disposed at the other end. The head of the plunger is disposed in substantially fluid sealing engagement with the interior surfaces of the barrel and as such will serve to force the contained fluid from a nozzle or other discharge port associated with the delivery end of the barrel as the plunger is compressed.

One important factor of the syringe assembly of the type described herein is the disposition and structure of the indicia assembly specifically including a plurality of measurement indicators which facilitate the accurate determination of the volume or quantity of the fluid disposed within the interior of the syringe barrel. The accuracy of such measurement indicators is important in order to dispense or deliver an appropriate quantity of medication or other fluid to a patient either directly or indirectly, such as through some type of additional fluid dispensing structure including, but not limited to an IV assembly.

Therefore, a feature of one or more embodiments of the syringe assembly of the present invention is the provision of an indicia assembly disposed and structured to provide an accurate determination of the quantity or volume measurement of the fluid within the interior of the syringe barrel. In addition, structural and operative features of the indicia assembly facilitate the visual observation thereof by incorporating a visually contrasting appearance of various operative portions of the indicia assembly, as set forth in greater detail hereinafter.

More specifically, the indicia assembly of the present invention comprises a first indicia section and a second indicia section each disposed on or in direct association with a common wall portion of the barrel. As at least one preferred embodiment of the indicia assembly is practically applied, each indicia section extends along an appropriate length on an exterior surface of the common wall portion of the barrel. As such, the quantity or the volume of the contained fluid within the interior of the barrel can be easily and accurately determined by viewing either of the first or second section of the indicia assembly. Moreover, each of the first and second indicia sections include a plurality of measurement indicators or measurement markings which are scaled or graduated to accommodate an accurate determination of volume measurement of the contained fluid. Accordingly, for purposes of clarity the first indicia section comprises first plurality of measurement indicators or measurement markings, while the second indicia section comprises a second plurality of measurement indicators or measurement markings. As will be more specifically outlined hereinafter, equivalent, corresponding ones of the first and second plurality of measurement markings will be disposed in aligned relation with one another on the common wall portion in order to provide an accurate, visual determination of the volume of the contained fluid within the syringe barrel by an individual, while viewing either the first indicia section or the second indicia section.

One or more preferred embodiments of the indicia assembly of the present invention also include the provision of a segregating section. The segregating section is disposed substantially "between" or in segregating relation to align and at least partially overlapping first and second indicia sections. Moreover, the structure of the segregating section is such as to be disposed in between equivalent or corresponding ones of the first and second plurality of markings of each of the first and second indicia sections. Structural and operative features of the segregating section includes its disposition and structuring to facilitate a visual segregation of the first and second plurality of measurement indicators or measurement markings extending along the outer surface of the common wall portion of the syringe barrel. As used herein, the term "visual segregation" and any reasonable equivalent thereof is meant to describe the inability of a single individual to concurrently view equivalent, corresponding, aligned ones of the first and second plurality of measurement markings. However, the structural and operative features of the indicia assembly of the present invention facilitates clear visual observation of either the first plurality of measurement indicators or measurement markings or the second plurality of measurement indicators or measurement markings dependent on the location and/or viewing direction or line of site of an individual when observing the indicia assembly and attempting to determine a measurement of the volume contained within the syringe barrel.

Accordingly, the cooperative structuring and disposition of the first and second indicia sections, specifically as they relate to the segregating section, allows for exclusive viewing of either the first indicia section or the second indicia section, but substantially restricts a concurrent viewing of both. More specifically, the first plurality of measurement markings associated with the first indicia section, are viewable through an interior of the barrel, whether or not the barrel contains a liquid. In contrast, the second indicia section, including the second plurality of measurement markings, is disposed and structured to be viewable only from an exterior of the syringe barrel along a line of sight directed towards the exterior surface of the common wall portion on which the indicia assembly is disposed. Accordingly, the concurrent viewing of at least equivalent, corresponding and/or aligned ones of the first and second plurality of measurement markings is prohibited or at least significantly restricted at least in part due to the disposition and visual segregating features of the segregation section, as generally set forth above.

Other structural and operative features associated with the cooperative nature of the first and second indicia sections and the segregating section is the provision of specifically contrasting appearances thereof. Accordingly, the color or other appearance features of the inner and outer surfaces of the segregating section, as it relates to the appearance or color of the first and second plurality of measuring markings are in stark contrast. As a result, a viewing of either the first or second indicia section respectively through the interior of the syringe barrel or along an exclusively exterior line of sight towards the exterior surface of the common wall portion, results in a visually distinct appearance of the first and second plurality of measurement indicators or measurement markings from the segregating section and the syringe assembly. Also, the structuring of the segregating section is such that an individual cannot view through the segregating section and cannot concurrently or simultaneously view both equivalent and/or aligned ones of the first and second measurement markings.

Therefore, the syringe assembly of the present invention and more specifically, the indicia assembly associated therewith provides clear, accurate, visual determination of the quantity and/or volume measurement of the liquid maintained within the barrel interior specifically, but not exclusively, as it relates to the position of the corresponding portion of the plunger which serves to regulate and/or drive the volume of contained fluid.

Yet another preferred embodiment of the syringe assembly of the present invention comprises the indicia assembly including at least one indicator disposed on the body. The at least one indicator is dimensioned and configured to extend along at least a length of a portion of the body which is intended to contain liquid contents within the interior of the barrel or body. As set forth above, such liquid contents is typically in the form of a liquid medication, saline solution, etc. More specifically, the at least one indicator included of the indicia assembly is structured to facilitate the detection of a void within the hollow interior of the body. As such, the "void" may comprise an empty space formed within or immediately adjacent to the liquid contents or on or contiguous to the exterior surface thereof.

For purposes of clarity it is emphasized that the term "empty space" is meant to describe the aforementioned "void" being completely or substantially empty of any type of liquid contents. As such, the "empty space" and "void" will be more commonly represented as an air bubble or gas bubble, wherein the void, while being considered empty of any liquid contents, does contain air or other gaseous fluid. As is well recognized in the medical field, harm may result if an injection is administered to a patient, when an air bubble exists within the syringe body such as within or contiguous to the liquid contents being administered. Accordingly, care is typically taken by the administering personnel to remove any type of air bubble or "void" from the interior of the syringe body and/or specifically from the liquid contents of the syringe body.

Therefore, the at least one indicator of this additional preferred embodiment of the indicia assembly comprises a predetermined structure and disposition which serves to distinguish and determine the existence of a void or air bubble relative to the liquid contents. More specifically, this distinguishing ability is at least partially based on facilitating the visual observation of the void. Moreover, once a visual determination of a void has been made the possibility of inadvertent injection or administering of the liquid contents of the syringe is eliminated or significantly reduced.

While this preferred embodiment of the indicia assembly includes at least one elongated indicator member, it is emphasized that a plurality of such indicators may also be concurrently mounted on or integrated within the body of the syringe. Moreover, each of the one or more indicator generally have an elongated, preferably linear configuration extending continuously along the length of at least the portion of the syringe body intended to contain liquid contents therein. Variations of the one or more indicators may include a continuous or overall structural configuration extending along the predetermined length of the body portion or a plurality of indicator segments spaced apart but linearly aligned, so as to collectively form an elongated array which forms the aforementioned elongated disposition over the intended body portion.

Also, all or different ones of the indicators may be disposed on the exterior surface of the body, the interior surface of the body or otherwise integrated, imbedded, etched or otherwise incorporated within the material of the body itself. Therefore, the structure of the one or more indicators is cooperative with the at least partially transparent material of the syringe body so as to facilitate the visual observation of the liquid contents within the body as well as the body interior. As a result, the ability to visually distinguish and thereby detect one or more voids within the syringe body and in relation to the liquid contents, as set forth above, is significantly enhanced.

Additional features of the one or more indicators included within the indicia assembly is the use thereof in combination with at least the first indicia section and the second indicia section disposed on a common wall portion of the body, as generally set forth above. Moreover, the one or more void detecting indicators of this embodiment of the indicia assembly can also be used in combination with a segregated section disposed and structured to at accomplish an at least partial visual segregation of the first and second indicia sections. As also set forth above the first and second indicia sections may include a plurality of measurement indicators or measurement markings disposed and structured to be viewable either through the interior of the syringe body or from the exterior thereof as explained in greater detail hereinafter.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 1 is a perspective view in schematic form of a syringe assembly of the present invention incorporating at least one preferred embodiment of the indicia assembly thereon.

FIG. 2 is a schematic, transverse sectional view, in exploded form, of the embodiment of FIG. 1.

FIG. 3A is a schematic, transverse sectional view of the embodiment of FIGS. 1 and 2 representing at least one line of sight for viewing a portion of the indicia assembly.

FIG. 3B is a schematic, front interior view in partial cutaway of a portion of the indicia assembly as viewed along the line of sight of FIG. 3A.

FIG. 4A is a schematic, transverse sectional view of the embodiment of FIGS. 1-3 representing an opposing line of sight for viewing the indicia assembly, from that represented in FIG. 3A.

FIG. 4B is a schematic, front view of the indicia assembly as viewed along the line of sight represented in FIG. 4A.

FIG. 8A is a schematic, transverse sectional view of a syringe body and representative indicia assembly of the embodiments of FIGS. 6 and 7, as viewed along an indicated line of sight.

FIG. 8B is a schematic, interior view showing the indicia assembly of the embodiment of at least FIG. 8A as viewed along the line of sight represented in FIG. 8A.

FIG. 9A is a schematic, transverse sectional view of yet another preferred embodiment of the indicia assembly.

FIG. 9B is a schematic, interior view of the embodiment of FIG. 9A as viewed along the represented line of sight of FIG. 9A.

Like reference numerals refer to like parts throughout the several views of the drawings.

DETAILED DESCRIPTION OF THE PREFERRED EMBODIMENT

Figure 5B:
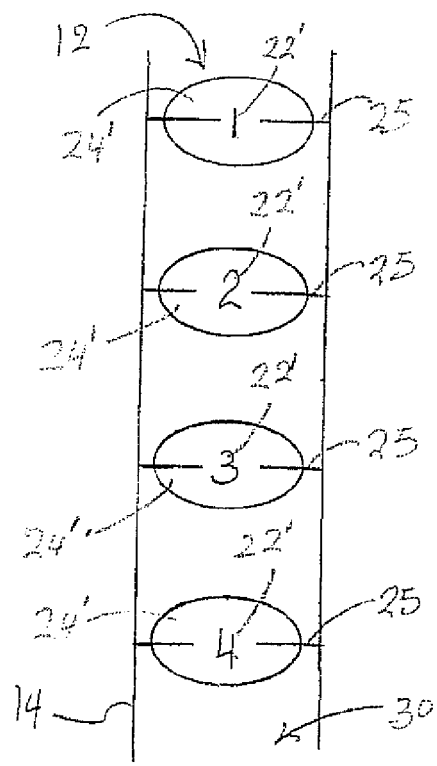
FIG. 5B is a schematic, front interior view in partial cutaway of a portion of the indicia assembly as viewed along the line of sight of FIG. 5A.

As shown in the accompanying drawings, the present invention is directed to a syringe assembly generally indicated as 10 having an indicia assembly generally indicated as 12 thereon. The syringe assembly 10 includes an elongated body or tubular barrel 14 having an at least partially hollow interior 14' and being at least partially formed from a transparent material. The syringe assembly 10 also includes a plunger structure generally indicated as 16 and including a plunger rod or like member 18 and a plunger head 20. In somewhat conventional fashion, the plunger head 20 is disposed in substantially fluid sealing relation with the interior surfaces of the barrel or body 14. As a result, reciprocal movement of the plunger rod 18 serves to facilitate the intake of a liquid composition into the interior of the barrel or body 14 and also serves to dispense the contained liquid composition from the interior 14' of the barrel 14, such as through a dispensing nozzle or discharge port generally indicated as 21.

Accordingly, one feature of at least one preferred embodiment of the present invention includes the indicia assembly 12 comprising a first indicia section 22, a second indicia section 23, and a segregating section 24. With primary reference to FIGS. 3B and 4B, the first indicia section 22 includes a plurality of measurement markings 22'. Somewhat similarly, the second indicia section 23 includes a second plurality of indicia markings 23'. Each of the first and second plurality of measurement markings 22' and 23' and the scale markings 25 associated therewith provide a visual indication of a measurement of the volume or quantity of the contents of the interior 14' of the barrel or body 14. As should be apparent, the alphanumeric characters included as part of the first and second plurality of measurement markings 22' and 23' may vary dependent at least on the size of the barrel 14, the type or purpose of the liquid composition to be dispensed from the syringe assembly 10 and/or the specific reason for the treatment of the individual or patient. As such, each of the first and second plurality of measurement markings 22' and 23' are generically represented only by the numerals 1-4. In addition, each of the first and second indicia sections 22 and 23 may include a plurality of scale markings or a graduated scale, as at 25, which are provided to further enhance the accuracy of the reading and the determination of the volume or quantity of composition contained within the interior 14' of the barrel 14. Also, as will be explained in greater detail hereinafter, at least one embodiment of the present invention includes the segregating section 24, including the opposite surfaces thereof having a white or lighter color and appearance. However, in order to provide a sufficiently contrasting appearance, the measurement markings 22' and 23' are darker in color and appearance than that of the white or lighter color of the segregating section surfaces.

In addition, each of the first and second indicia sections 22 and 23, as well as the first and second plurality of measurement markings 22' and 23' respectively associated therewith are mounted on and extend along what may be generally considered as a common wall portion, generally indicated as 30, of the barrel 14. Similarly, the segregating section 24 is also mounted on or in direct association with the common wall portion 30 and is disposed substantially between the first indicia section 22 and the second indicia section 23. As will be explained in greater detail hereinafter, the segregating section 24 is structured so as to "visually segregate" the first and second indicia sections 22 and 23 and more specifically the measurement markings 22' and 23' including the associated numerals or characters respectively associated therewith. In at least one preferred embodiment, such a "visual segregation" will effectively prohibit the concurrent viewing of at least aligned ones of the measurement markings 22' and 23' from a common location or along a common line of sight. Therefore, at least a portion of the segregating section 24, such as at least a plurality of segregating segments 24' may be formed from an at least partially opaque and/or other material which restricts the concurrent viewing of overlying or aligned, characters or numerals 1-4 defining the corresponding measurement markings 22' and 23' and the scale markings 25 associated therewith. As a result, when a user of the syringe assembly 10 is viewing the indicia assembly 12 along substantially opposing lines of sight 40 and 42, the individual will be unable to concurrently "read" overlapping or correspondingly disposed, aligned ones of the measurement markings 22', 23'.

The structural and operative features of the indicia assembly 12 may be further defined by their relative disposition. More specifically, as represented in FIGS. 3A, 4A and 5A first indicia section 22, including each of the measurement markings 22', is disposed in substantially confronting relation to an exterior or other appropriate part of the common wall portion 30. In cooperation therewith, the segregating section 24 is disposed in "overlying" or covering relation to the first indicia section 22. As such, each of the segregating segments 24' is disposed in overlying relation to a different one of the plurality of measurement markings 22' with which it is aligned. Further structural cooperation of the various components of the indicia assembly 12 include the second indicia section 23, as well as the measurement markings 23' associated therewith, being disposed in overlying relation to the segregating section 24 and in at least partially visually and possibly physically segregated relation to the first indicia section 22.

Figure 5A:
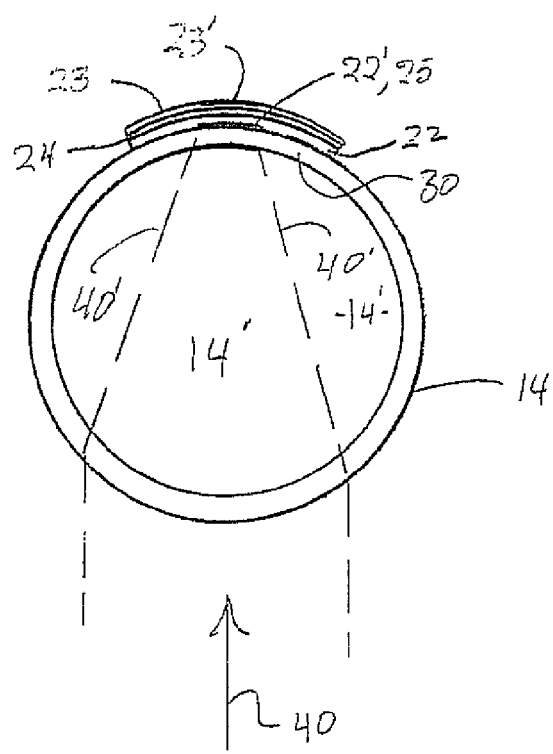
FIG. 5A is a schematic, transverse sectional view of the embodiment of FIGS. 1-4 representing at least one line of sight for viewing a portion of the indicia assembly when the syringe barrel contains a liquid.

However, as best demonstrated in FIGS. 3-5, corresponding ones of the scale markings 25 are disposed in direct aligned relation with one another, so as to indicate the same volume measurement whether viewing the barrel 14 along line of sight 40 or 42. In contrast, the numerals or characters "1-4" defining the measurement markings 22' and 23' may be at least minimally off-set from one another as evident from a comparison of the numerals of the measurement markings 22' and 23' in FIGS. 1, 3B, 4B and 5B. More specifically, the numerals of the measurement markings 22' of the first indicia section 22, as represented in FIGS. 3B and 5B are preferably located above or out of direct alignment with the corresponding scale markings 25. This is at least partially due to the fact the interior of the barrel 14 will be commonly viewed, along line of sight 40, when it is in the orientation represented in FIG. 1, wherein the discharge port 21 is facing in a generally upward direction. However, when viewing from the exterior of the barrel 14, along line of sight 42 the numerals "1-4" defining the measurement markings 23' of the second section 23 will be observed in general alignment with the scale markings 25, as represented in FIGS. 1 and 4B.

Accordingly, this at least partial off-set relation of the characters of the measurement markings 22' and 23' defines a cooperative structuring with the at least partially opaque and white or lightly colored appearance of the segregating section 24, including the opposite surfaces thereof. As a result the black or darker colored plunger head 20 will always be positioned relative to the measurement markings 22' and 23' to allow a clear and unobstructed viewing and reading of the measurement markings 22' and 23'. More specifically, when viewing along line-of-sight 40, the measurement markings 22' will always be disposed above the corresponding scale markings 25 and the plunger head 20 aligned with the associated scale marking 25. When viewing along the line-of-sight 42, the at least partially opaque and lightly colored segregating section segment 24' will visually "block out" any portion of the plunger head 20 which is aligned with a correspondingly positioned measurement marking 23'. However, the alignment of the plunger head 20 with the corresponding scale marking 25 will be clearly viewable due to the size and position of the corresponding segment 24' and the fact that the scale markings 25 may extend substantially entirely around the barrel 14.

Therefore, an accurate determination of the volume or quantity of the liquid composition maintained within the interior 14' of the barrel or body 14 is assured, regardless of an individual viewing along the line of sight 40 or line of sight 42. Moreover, the at least partially opaque or other material from which the segregating segments 24' are formed will accomplish the aforementioned "visual segregation" of aligned ones of the measurement markings 22' and 23'. Also, aligned ones of the first and second plurality of measurement markings 22' and 23' are viewed from opposing or at least different interior and exterior lines of sights 40 and 42, and will be reversely oriented.

Additional structural and operative features of the present invention, specifically relating to the indicia assembly 12 is the interior and exterior surfaces of the portions of the segregating section 24 disposed in aligned relation with the measurement markings 22' and 23'. More specifically, the segregating segments 24' have a contrasting visual appearance or coloring as compared to the coloring or appearance of the correspondingly disposed measurement markings 22' and 23'. By way of example only, in one preferred embodiment of the indicia assembly 12, both the inner and outer surfaces of each of the segregating segments 24' are white in color thereby providing a stark visual contrast to the black or other more darkened color of the measurement markings 22' and 23'.

With further reference to FIGS. 3-5, the structural and operative features of the indicia assembly 12 facilitate the exclusive viewing or reading of the indicia assembly 22 as well as the measurement markings 22' associated therewith along the line of sight 40. It is specifically indicated that the line of sight 40 looks through the interior of 14' of the tubular body or barrel 14 towards and at least partially through the common wall portion 30 which is directly associated with the indicia assembly 12. The results of such visual observation along line of sight 40 will result in an individual being able to only view the plurality of measurement markings 22' defining the first indicia section 22. Also, the contrasting appearance of the corresponding inner surface of each of the segregating segments 24' will facilitate the viewing of the contrasting colored measurement markings 22'.

In contrast, an individual may view the indicia assembly 12 from a substantially opposing line of sight, as at 42, relative to the line of sight 40 and from an exterior side of the barrel 14. As such when viewing along line of sight 42, the individual will be able to exclusively read or view the second indicia section 23 comprising the measurement markings 23'. As with the embodiment of FIGS. 3A and 3B, the measurement markings 23' will be more visually available due to the white coloring or contrasting coloring of the outer or exterior surface of each of the segregating segments 24'.

At least one operative feature of the indicia assembly 12 is demonstrated in FIGS. 5A and 5B. Accordingly, when viewing the indicia section 22 and the associated measurement markings 22' along the line of the sight 40 a magnification of the measurement markings 22' will be evident as schematically represented in phantom lines 40' due to the inherent magnification characteristics of a transparent or translucent liquid when such liquid composition is present within the interior 14' of the barrel 14. When the barrel 14 is at least partially filled and when the line of sight 40 extends through the filled interior portion 14' of the barrel 14, the appearance of the indicia section 22, specifically including the measurement markings 22' associated therewith will appear to be enlarged.

It is emphasized that the formation, structure, disposition, etc. of the measurement markings 22', 23' and the segregating markings 24' may vary and include, but not be limited, to appropriate techniques associated with the printing, etching, painting, embossing, etc., thereof on or in direct association with the common wall portion 30. Accordingly their relative and cooperative placement such as being disposed in aligned, over lapping, and or covering relation to one another, as set forth above, should be considered in this context. Further, the first indicia section 22, second indicia section 23 and segregating section 24 as well as the measurement markings 22', 23' and segregating segments 24' respectively associated therewith may be at least partially or entirely integrated with one another or be independently structured and/or applied.

Yet additional preferred embodiments of the indicia assembly are represented in FIGS. 6 through 9. More specifically, the indicia assembly 12 disclosed in the embodiments of FIGS. 1 through 5 are correspondingly represented and comprise a first indicia section 22 a second indicia section 23 and a segregating section 24 as described herein with reference to FIG. 2. Moreover, the first indicia section 22 includes a plurality of measurement indicators or measurement markings 22'. Similarly, the second indicia section 23 includes a second plurality of indicia indicators or indicia marking 23'.

However, with primary reference to FIGS. 6A, 6B and 7A, 7B, the additional preferred embodiment of the indicia assembly is represented as 112 and includes at least one elongated indicator 114. As will be explained in greater detail with specific referenced to FIGS. 8A, 8B and 9A, 9B, the indicia assembly 112 can include one or more elongated indicators 114 and 114'. Further, the one or more indicators, 114 may include an elongated, contiguous structural configuration extending along the length of at least a portion of the syringe body or barrel 14 which is normally intended to contain the liquid contents of the body 14. In contrast, the elongated structural configuration of the one or more indicators 114' may be defined by a plurality of indicia segments 114" collectively disposed in an elongated, preferably but not necessarily, linear array, schematically represented in FIG.

9B. Also, the disposition of one or more indicators 114 and 114' may be on the interior or exterior surfaces of the syringe body or barrel 14 or alternatively may be embedded, etched, molded, or otherwise appropriately integrated or incorporated within the walls of the syringe body 14.

Figure 6B:
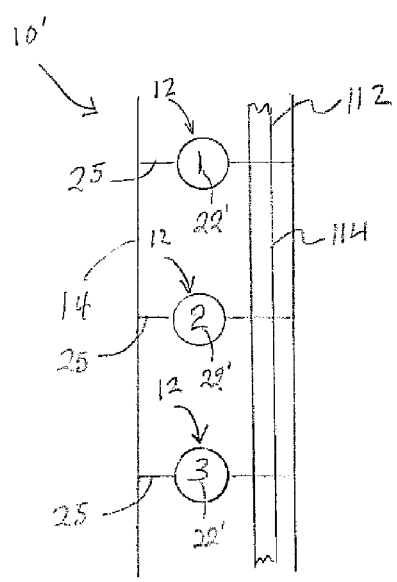
FIG. 6B is a schematic, partial cutaway interior view of the preferred embodiment of FIG. 6A, as viewed along the indicated line of sight.
Figure 7B:
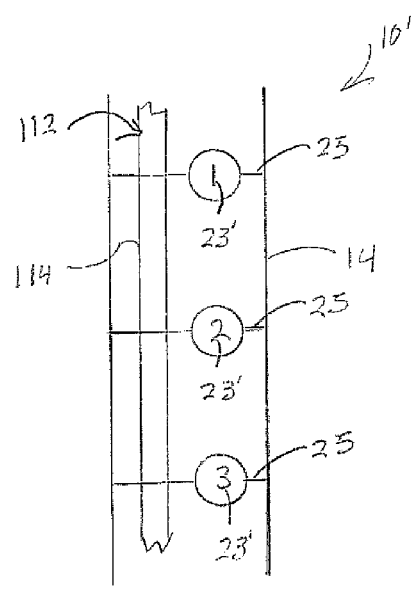
FIG. 7B is a schematic, front exterior view of the indicia assembly of the embodiment of FIG. 7A, as viewed along the indicated line of sight.
Figure 6A:
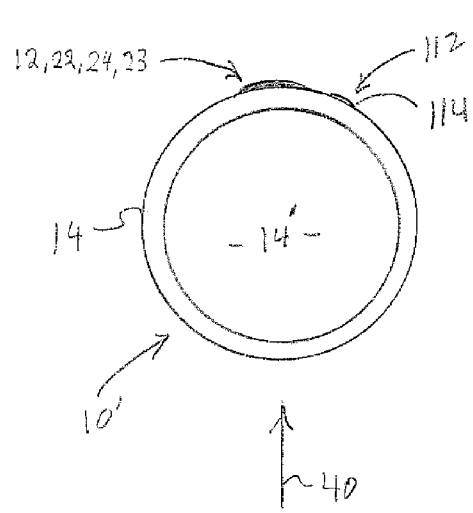
FIG. 6A is a schematic, transverse sectional view of another preferred embodiment of the indicia assembly.
Figure 7A:
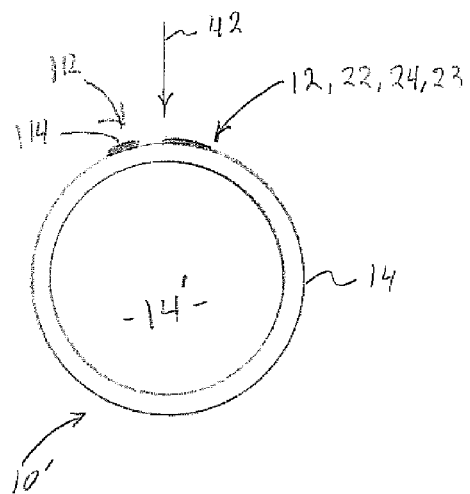
FIG. 7A is a schematic, transverse sectional view of the embodiment of FIGS. 6A and 6B representing an opposing line of sight from that represented in FIG. 6A.

In a preferred application of the additional indicia assembly 112, it may be used in combination with the indicia assembly 12, which as set forth above, has the structural and operative features as described in detail and schematically represented at least in FIG. 2. As indicated in FIGS. 6A and 6B, the at least one indicator 114 may be concurrently observed with the measurement markings or measurement indicators 22' of the first indicia section 22 when viewing along line of sight 40, through the interior 14' of the syringe body 14. In contrast and as represented in FIGS. 7A and 7B, when viewing along the line of sight 42, the indicator 114 will be concurrently observed with the indicia assembly 12 represented by the second indicia section 23 and the corresponding plurality of measurement indicators or measurement markings 23'. It should further be noted that in FIGS. 6B and 7B the scale markings 25 are also viewed in combination with the first and second indicia sections 22 and 23 concurrently with the indicia assembly 112 and/or at least the one indicator 114.

At least one purpose of providing the additional preferred indicia assembly 112 including the one or more indicators, 114, 114', etc. is that each indicator(s) 114, 114' are structured to facilitate the detection of a void 120 within the hollow interior 114' of the syringe body 14, as schematically represented in 8A, 8B and 9A, 9B. Moreover, the one or more indicators 114 comprise a predetermined structure which is operative to visually distinguish the void 120 from the liquid contents of the syringe body or barrel 14. To enhance visual detection and determination of a void 120, each of the one or more indicators 114, 114' may have a visually contrasting appearance to the liquid contents of the body. This contrasting appearance may be defined by a black or darker coloring of at least a portion of the one or more indicators 114, 114'.

As further represented in FIGS. 8A and 9A when viewing along the respective lines of sight 40' and 40" the user of the syringe is in effect viewing through the interior 14' and through the liquid contents therein. As a result, an optical distortion may occur when a void 120 is present, as schematically represented in FIGS. 8B and 9B. As set forth above, the indicator 114 comprises a continuous, elongated structural configuration. In contrast the indicator 114' comprises a plurality of indicator segments 114" collectively arranged in an elongated, preferably linear array. In either of these structural modifications of the indicator 114, 114', the visual distortion may occur when viewing along the respective lines of sight 40' and 40" such that at least a portion of the respective indicators 114 and/or 114' are being viewed at least partially through the void.

For purposes of clarity the term "void" as applied to schematic representation 120 is in fact an empty space or more specifically a space occupied primarily by air or other gaseous fluid. Such voids are perhaps more commonly referred to as "air bubbles" and must be removed from the liquid contents of the syringe body 14, as well as the body interior 14', prior to the administering the contents, as also set forth above.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A syringe assembly comprising:
   an elongated body having a hollow interior portion and being at least partially formed from a transparent material and intended for containment of liquid contents,
   an indicia assembly including at least one indicator formed on said elongated body,
   said at least one indicator structured to facilitate detection of a void in said liquid contents within said hollow interior portion of said elongated body wherein said void comprises an air bubble,
   said at least one indicator comprising a predetermined structure comprising an elongated configuration disposed at least along a length of a portion of said elongated body intended for containment of the liquid contents and operative to distinguish by an optical distortion the void from the liquid contents of said elongated body wherein said optical distortion comprises said elongated configuration appearing disjointed,
   said indicia assembly further including at least a first indicia section comprising an inner surface, an outer surface and a thickness therebetween and a second indicia section comprising an inner surface, an outer surface and a thickness therebetween; each of said first and second indicia sections disposed on a common wall portion of the elongated body,
   said indicia assembly further comprising a segregating section comprising an inner surface, an outer surface and a thickness therebetween disposed and structured for at least partial visual segregation of said first and second indicia sections,
   said first indicia section including a plurality of volume indicating measurement markings disposed and structured to be viewable through an interior of said elongated body,
   said second indicia section including a second plurality of volume indicating measurement markings disposed and structured to be viewable in a direction toward a corresponding exterior surface of said common wall portion,
   said segregating section disposed and structured to restrict concurrent viewing of at least correspondingly positioned ones of said first and second plurality of measurement markings, and
   said at least one indicator disposed for concurrent viewing thereof with at least one of said first and second indicia sections.

2. A syringe assembly as recited in claim 1 wherein said first plurality of measurement markings are disposed and structured to be viewable from an exterior of said elongated body along a line of sight directed through said exterior of said elongated body towards an interior surface of said elongated body; said at least one indicator disposed for concurrent viewing thereof with said first plurality of measurement markings.

3. A syringe assembly as recited in claim 1 wherein said second plurality of measurement markings are disposed and structured to be viewable from an exterior of said elongated body along a line of sight directed towards a corresponding exterior surface of said elongated body; said at least one indicator disposed for concurrent viewing thereof with said first and second plurality of measurement markings.

4. A syringe assembly as recited in claim 1 wherein said indicia assembly further comprises a plurality of indicators disposed on said elongated body in laterally spaced relation to one another; each of said plurality of indicators extending along at least a portion of said elongated body intended for containment of the liquid contents.

5. A syringe assembly as recited in claim 4 wherein said first plurality of measurement markings are disposed and structured to be exclusively viewable through an interior of said elongated body; at least one of said plurality of indicators disposed for concurrent viewing thereof with said first plurality of measurement markings.

6. A syringe assembly as recited in claim 5 wherein said second plurality of measurement markings are disposed and structured to be viewable from an exterior of said elongated body along a line of sight directed towards a corresponding exterior surface of said elongated body; at least one of said plurality of indicators disposed for concurrent viewing thereof with said second plurality of measurement markings.

7. A syringe assembly as recited in claim 4 wherein at least one of said plurality of indictors comprises an elongated, continuous configuration disposed on and extending along a length of said elongated body.

8. A syringe assembly as recited in claim 7 wherein at least one of said plurality of indicators comprises a plurality of indicator segments collectively defining an elongated array disposed on and extending along at least a portion of said elongated body intended for containment of the liquid contents.

9. A syringe assembly as recited in claim 1 wherein said segregating section comprises a plurality of segregating segments each disposed in visually segregating relation at least between said correspondingly positioned ones of said first and second plurality of measurement markings.

10. A syringe assembly as recited in claim 9 wherein at least some of said plurality of segregating segments are at least partially opaque and include an inner surface and outer surface; said inner surface disposed in confronting relation to correspondingly disposed ones of said first plurality of measurement markings, said outer surface disposed in confronting relation to correspondingly disposed of ones of said second plurality of measurement markings.

11. A syringe assembly as recited in claim 9 wherein each of said inner and outer surfaces includes opacity and a contrasting visual appearance, relative to correspondingly disposed one of said first and second plurality of measurement markings and a plunger head of the syringe assembly to facilitate viewing of said first and second plurality of measurement markings.

* * * * *